US008703649B2

(12) United States Patent
Israels et al.

(10) Patent No.: US 8,703,649 B2
(45) Date of Patent: Apr. 22, 2014

(54) PESTICIDAL SUSPO-EMULSION COMPOSITIONS

(75) Inventors: Rafel Israels, Köln (DE); Katharine Klamczynski, Böhl-Iggelheim (DE); Marco Kuhns, Haβloch (DE); Ulf Schlotterbeck, Mannheim (DE)

(73) Assignee: BASF SE, Ludwigshafen (DE)

( * ) Notice: Subject to any disclaimer, the term of this patent is extended or adjusted under 35 U.S.C. 154(b) by 31 days.

(21) Appl. No.: 13/387,273

(22) PCT Filed: Jul. 20, 2010

(86) PCT No.: PCT/EP2010/060463
§ 371 (c)(1), (2), (4) Date: Jan. 26, 2012

(87) PCT Pub. No.: WO2011/012493
PCT Pub. Date: Feb. 3, 2011

(65) Prior Publication Data

US 2012/0122682 A1 May 17, 2012

Related U.S. Application Data

(60) Provisional application No. 61/309,004, filed on Mar. 1, 2010.

(30) Foreign Application Priority Data

Jul. 28, 2009 (EP) .................................... 09166627

(51) Int. Cl.

| | |
|---|---|
| ***A01N 25/26*** | (2006.01) |
| ***A01N 25/00*** | (2006.01) |
| ***A61K 31/41*** | (2006.01) |
| ***A01N 43/48*** | (2006.01) |
| ***A01N 43/00*** | (2006.01) |
| ***A01N 43/34*** | (2006.01) |

(52) U.S. Cl.
USPC ........... 504/100; 514/399; 514/407; 514/269; 514/383; 514/422; 514/355; 514/538; 514/539

(58) Field of Classification Search
None
See application file for complete search history.

(56) References Cited

U.S. PATENT DOCUMENTS

| | | | |
|---|---|---|---|
| 4,245,321 A | 1/1981 | Gennetten | |
| 4,272,417 A | 6/1981 | Barke et al. | |
| 4,339,456 A | 7/1982 | Rushing | |
| 4,372,080 A | 2/1983 | Rushing | |
| 4,383,391 A | 5/1983 | Thomas et al. | |
| 4,634,587 A | 1/1987 | Hsiao | |
| 4,735,014 A | 4/1988 | Weber | |
| 5,300,127 A | 4/1994 | Williams | |
| 5,328,942 A | 7/1994 | Akhtar et al. | |
| 5,580,544 A | 12/1996 | Dao et al. | |
| 5,622,003 A | 4/1997 | Narayanan | |
| 5,661,103 A | 8/1997 | Harms et al. | |
| 5,791,074 A | 8/1998 | Pryor | |
| 5,834,447 A | 11/1998 | Phillion et al. | |
| 5,849,320 A | 12/1998 | Turnblad et al. | |
| 5,876,739 A | 3/1999 | Turnblad et al. | |
| 5,882,713 A | 3/1999 | Eskins et al. | |
| 5,939,356 A | 8/1999 | Wellinghoff | |
| 6,365,614 B1 | 4/2002 | Schelberger et al. | |
| 6,410,481 B1 * | 6/2002 | Rochling et al. | 504/144 |
| 2006/0171979 A1 | 8/2006 | Calvo et al. | |
| 2006/0199736 A1 | 9/2006 | Vasek | |
| 2008/0318791 A1 | 12/2008 | Baur et al. | |

FOREIGN PATENT DOCUMENTS

| | | |
|---|---|---|
| WO | WO 02102148 A2 * | 12/2002 |
| WO | WO 03/075657 | 9/2003 |
| WO | WO 2005/074685 | 8/2005 |
| WO | WO 2007/028538 | 3/2007 |
| WO | WO 2007/054469 | 5/2007 |
| WO | WO 2008/096005 | 8/2008 |

OTHER PUBLICATIONS

Alanwood, “Pyraclostrobin”, <http://www.alanwood.net/pesticides/pyraclostrobin.html>, Apr. 4, 2005, p. 1.*
Bayer CropSciences, “Suspoemulsions (SE)”, <http://www.bayercropscience.com.mx/Formulierung/Formulierung_en/daten/flash_formulierung.html>, Nov. 24, 2007, p. 1.*
“Diamant®”, Oct. 16, 2008, XP002558984, Search Report.
International Search Report, PCT/EP2010/060463, Aug. 22, 2011.
International Preliminary Report on Patentability, PCT/EP2010/060463, Apr. 13, 2012.

* cited by examiner

*Primary Examiner* — Tracy Vivlemore
*Assistant Examiner* — Monica Shin
(74) *Attorney, Agent, or Firm* — Brinks Gilson & Lione

(57) ABSTRACT

The present invention relates to formulation comprising at least (i) two pesticidal compounds A and B dissolved in a lactic acid ester and wherein a) both A and B have melting points below 900 C b) both A and B are selected from the following list: pyraclos-trobin, metalaxyl, mefenoxam, tri-floxystrobin, imazalil, pro-chloraz and ipconazole with the proviso that A is different from B (ii) at least one pesticidal compound C present in solid particles, and having a melting point of 900 C and above, and to their use as seed treatment formulation as well as their use for plant protection, including seed and crop protection.

20 Claims, No Drawings

PESTICIDAL SUSPO-EMULSION COMPOSITIONS

This application is a National Stage application of International Application No. PCT/EP2010/060463 filed Jul. 20, 2010, which claims the benefit of U.S. Provisional Application No. 61/309,004, filed Mar. 1, 2010, the entire contents of which are hereby incorporated herein by reference. This application also claims priority under 35 U.S.C. §119 to EP Patent Application No. 09166627.1, filed Jul. 28, 2009, the entire contents of which is hereby incorporated herein by reference.

The present invention relates to aqueous suspo-emulsions (SE) formulations containing at least three fungicidally active compounds and to their use as seed treatment formulation as well as their use for plant protection, including seed and crop protection.

Pesticide compounds are often applied in the form of a dilute aqueous composition in order to achieve a good interaction with the target organism, such as plants, fungi and insects. However, most active compounds that are used as pesticides, in particular fungicidally active compounds, are only sparingly or even insoluble in water, i.e. they usually have a water-solubility of not more than 50 g/l.

Therefore, formulators are often confronted with difficulties in formulating pesticide compounds in stable formulations that can be easily stored for a long time and which still have a high stability and effective activity until end use. This problem especially occurs if more than two actives compounds are present in the composition.

WO 03/075657 relates to the use of lactic ester as crystallization inhibitors during application. The lactic acid esters are used in order to inhibite the presence of solid particles in pesticidal composition during application, assuring thus a better fluidity by spraying a liquid composition onto the plant.

WO 07/028538 relates to the use of different lactic ester in different agricultural pesticidal formulation for improving the action of agricultural pesticides on the level of plants.

WO 2005/074685 relates to the use of plant protection compositions comprising among other 2-ethylhexyl lactate for the control of harmful organism in paddy rice crops.

The above patents focus on the function of lactates to improve the applicability of formulations.

In many multi-component recipes, especially when high-melting active ingredients need to be combined with low-melting actives, a suspo-emulsion is the only feasible formulation type. Such a suspo-emulsion may comprise two fungicides A and B soluted in a selected organic solvent and a third pesticidally active compound C simultaneously present in form of solid particle, all components coexisting in a stable form. One critical aspect of the suspo-emulsion is the choice of solvent, as this solvent faces several requirements. On the one hand it should dissolve the low-melting actives, on the other hand it may not cause Ostwald-ripening of the high-melting actives.

We now found surprisingly that lactates are very well suited to this formulation type, especially if more than one low-melting active needs to be formulated.

The present invention relates to pesticidal suspo-emulsion composition comprising (i) two pesticidal compounds A and B dissolved in a lactic acid ester and wherein
  a) both A and B have melting points below 90° C.
  b) both A and B are selected from the following list: pyraclostrobin, metalaxyl, mefenoxam, trifloxystrobin, imazalil, prochloraz and ipconazole with the proviso that A is different from B, (ii) at least one pesticidal compound C present in solid particles, and having a melting point of 90° C. and above, (iii) water, (iv) and optionally formulation auxiliaries.

The compositions of the present invention have been surprisingly found to provide suspo-emulsion (SE) formulations that contain water as continuous phase, two fungicidally active compounds A and B soluted in a lactic acid ester as organic solvent and a third pesticidal active compound C in form of dispersed particles, enabling an improved fungicidal activity of said compositions.

As used herein, "pesticidal compounds" or "active compound" or "compounds" is a compound which directly exerts a biologically relevant effect, preferably a pesticidal effect and more preferably a fungicidal effect.

The invention further relates to the use of compositions for the treatment of seeds, to methods of combating phytopathogenic fungi, a method of controlling undesired vegetation and methods of improving the health of plants based on the aforementioned compositions.

Surprisingly, it has been found that a composition which comprises the fungicidal compounds A, B characterised in that they have a melting point below 90° C., a third fungicidally active compound C in solid form and having a melting point being equal or above 90° C., in a selected organic solvent as solubilizing agent for the compounds A and B, water as continuous phase, a dispersing agent that keeps the hydrophobic particles suspended in water, form a stable suspension of the particles of compound C in an emulsion containing the dissolved fungicidally active compounds A and B.

The appropriate organic solvent according to the present invention must be able to prevent the formation of crystal when solving the two fungicidal components A and B and simultaneously must not solve the third component C which has to be present in the composition as solid particles. This selected solvent must therefore completely solute the component A and B in the emulsion droplet in a first time and further ensure the stability of the finished suspoemulsion formulation containing the dispersed third component C which is in solid form.

It has been surprisingly found that the appropriate organic solvents according to the invention are lactic acid esters. The lactic acid esters according to the present invention show a stabile distribution of the rates of the droplets and the particles sizes in the emulsion over variation of the temperature and this even over long storage. By using the lactic acid esters of the invention, the storage stability of the formulation composition of the present invention is enhanced. The use of the lactic acid esters according to the invention permits to obtain a composition wherein the two fungicidal compounds coexist with a third pesticidal compound present in solid form in such a way that the distribution of the droplets from the two fungicidal compounds soluted in the lactic acid ester and the solid particles of the third fungicidally compounds are homogeneously distributed in the suspoemulsion composition.

Further, it has been found that the physical states of the actives ingredients are maintained after long storage, thus affording sprayable liquid containing the solubilised compounds A and B in the lactic acid ester and fine particles of the third fungicidally active compound C When the terms lactic acid esters are used throughout the description, it is meant to include both optical isomers as well as mixtures thereof.

According to a preferred embodiment of the present invention, the preferred lactic acid esters for the practice of the invention are lactic acid esters of $C_4$ to $C_{12}$ saturated and unsaturated alkyl, $C_4$ to $C_{12}$ saturated and unsaturated cyclically $C_4$ to $C_{12}$ saturated and unsaturated branched alkyl lactic esters and mixtures thereof.

Particularly preferable lactic acid esters are 2-ethyl hexyl lactate, cyclohexyl lactate, 2-methylcyclohexyl lactate, heptyl lactate, octyl lactate and mixtures thereof.

More particularly preferable lactic acid ester is 2-ethylhexyl lactate (EHL) which is an ester of 2-ethylhexanol with lactic acid, preferably L-(+)-lactic acid, such as is obtainable, for example, as Purasolv® EHL from Purac Bioquimica (Gran Vial 19-25, 08160 Montmelo-Barcelona, Spain) or Purac Biochem (Gorinchem, NL).

Compounds A and B according to the present invention are selected fungicidally active compounds. Compounds A and B are fungicides selected from the group of pyraclostrobin, metalaxyl, mefenoxam, trifloxystrobin, imazalil, prochloraz and ipconazole with the proviso that A is different from B.

Compound C according to the present invention is a pesticidal active compound. In particular, compound C is a fungicide selected from the following list. The following list of active compounds C, in conjunction with which the compounds according to the invention can be used, is intended to illustrate the possible combinations but does not limit them. The following may be mentioned as examples of compounds C:

Azoxystrobin, boscalid, or compounds of the following groups:

a) Azoles:

triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-(4-chloro-phenyl)-2-([1,2,4]triazol-1-yl)-cycloheptanol;

imidazoles: cyazofamid, imazalil, pefurazoate, prochloraz, triflumizol;

benzimidazoles: benomyl, carbendazim, fuberidazole, thiabendazole;

others: ethaboxam, etridiazole, hymexazole and 2-(4-chloro-phenyl)-N-[4-(3,4-dimethoxy-phenyl)-isoxazol-5-yl]-2-prop-2-ynyloxy-acetamide;

b) Heterocyclic compounds:

pyridines: fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine, 2,3,5,6-tetra-chloro-4-methanesulfonyl-pyridine, 3,4,5-trichloropyridine-2,6-dicarbonitrile, N-(1-(5-bromo-3-chloro-pyridin-2-yl)-ethyl)-2,4-dichloronicotinamide, N-[(5-bromo-3-chloro-pyridin-2-yl)-methyl]-2,4-dichloro-nicotinamide;

pyrimidines: bupirimate, cyprodinil, diflumetorim, fenarimol, ferimzone, mepanipyrim, nitrapyrin, nuarimol, pyrimethanil;

piperazines: triforine;

pyrroles: fenpiclonil, fludioxonil;

morpholines: aldimorph, dodemorph, dodemorph-acetate, fenpropimorph, tridemorph;

piperidines: fenpropidin;

dicarboximides: fluoroimid, iprodione, procymidone, vinclozolin;

non-aromatic 5-membered heterocycles: famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester;

others: acibenzolar-S-methyl, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole, 5-chloro-7-(4-methylpiperidin-1-yl)-6-(2,4,6-trifluorophenyl)[1,2,4]triazolo[1,5-a]pyrimidine and 5-ethyl-6-octyl[1,2,4]triazolo[1,5-a]pyrimidine-7-ylamine;

Particular preferred compounds C according to the invention are azoxystrobin or boscalid or compounds of the azoles group, e.g. triticonazole, fludioxonil.

The compositions according to the present invention are at least ternary mixtures, i.e. compositions according to the invention comprising one fungicidally compound A (component 1), a first further fungicidally active compound B (component 2) and a second further pesticidal active compound C (component 3).

Preference is particularly given to suspoemlusion compositions comprising a compound A as component 1 being pyraclostrobin, a compound B as component 2 selected from the group of metalaxyl, mefenoxam, trifloxystrobin, imazalil, prochloraz and ipconazole and a compound C as component 3 selected from azoxystrobin, or boscalid, or triticonazole or fludioxonil.

Preference is particularly given to suspoemlusion compositions comprising a compound A as component 1 being pyraclostrobin, a compound B as component 2 selected from the group of metalaxyl, mefenoxam, trifloxystrobin, imazalil and ipconazole and a compound C as component 3 selected from azoxystrobin, or boscalid, or triticonazole or fludioxonil.

Preference is particularly given to formulation compositions comprising a compound A as component 1 being pyraclostrobin and a compound B as component 2 being metalaxyl and a compound C as component 3 selected from azoxystrobin, or boscalid, or triticonazole or fludioxonil.

Accordingly, in a more preferred embodiment, the present invention furthermore relates to compositions comprising a compound A as component 1 being pyraclostrobin and a compound B as component 2 being metalaxyl and a compound C as component 3 which is azoxystrobin.

Accordingly, in a more preferred embodiment, the present invention furthermore relates to compositions comprising a compound A as component 1 being pyraclostrobin and a compound B as component 2 being metalaxyl and a compound C as component 3 which is fludioxonil.

Accordingly, in a more preferred embodiment, the present invention furthermore relates to compositions comprising a compound A as component 1 being pyraclostrobin and a compound B as component 2 being metalaxyl and a compound C as component 3 which is boscalid.

Accordingly, in a more preferred embodiment, the present invention furthermore relates to compositions comprising a compound A as component 1 being pyraclostrobin and a compound B as component 2 being metalaxyl and a compound C as component 3 which is triticonazole.

The active compounds referred to as components 1, or 2, or 3, their preparation and their activity against harmful fungi is known (cf.:http://www.alanwood.net/pesticides/); these substances are commercially available. The compounds described by IUPAC nomenclature, their preparation and their fungicidal activity are also known (cf. Can. J. Plant Sci.

48(6), 587-94, 1968; EP 141317; EP 152031; EP 226917; EP 243970; EP 256503; EP 428941; EP 532022; EP 1028125; EP 1035122; EP 1201648; EP 1122244, JP 2002316902; DE 19650197; DE 10021412; DE 102005009458; U.S. Pat. No. 3,296,272; U.S. Pat. No. 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624).

The compositions of the present invention may optionally contain further formulation auxiliaries such as emulsifier dispersing agent, antifreeze agent, antifoam, thickener and binders in case of application in seeds.

In a preferred embodiment, a particular dispersing agent that has the capability to keep the hydrophobic particles suspended in water is Atlox 4913.

The term formulation auxiliaries refer to compounds or combinations of compounds which do not exert a biologically relevant effect of their own, but support the effects of the active compounds. Theses formulations auxiliaries are known to a person skilled in the art and are described for example in "crystalline complexes of agriculturally active organic compounds" (WO 2008/096005)

Preferably if present, the formulation auxiliaries comprise at least 0.5% based on the total amount of the composition of the present invention.

The formulation composition according to the invention can be prepared as follows: Compounds A and B are first soluted in the lactic acid ester, preferably EHL to form the solution S. This solution S is emulsified into water by mixing it with water and emulsifying agents and applying shear to arrive at the emulsion E with a droplet size <10 μm. Compound C is dispersed in water by mixing with dispersing agents and water and milling on bead-mill to a median particle size less than 10 μm, preferably less than 2 μm to form dispersion D. Finally, Emulsion E and Dispersion D are mixed by stirring and further auxilliaries like antifreeze, thickener, binder, etc. may be added.

The amount of the lactic acid ester solvent in the suspoemulsion composition according to the invention generally depends on the amount of compounds A and B. In general, the weight ratio of the lactic acid ester solvent to the compounds A and B together is from 1:1 to 10:1. The total amount of the lactic acid ester will be generally in the range of 2 to 40% by weight, in particular from 5 to 20% based on the total weight of the formulation.

In a particularly preferred embodiment, the amount of EHL in the suspoemulsion composition according to the invention generally depends on the amount of compounds A and B. In general, the weight ratio of EHL to the compounds A and B together is from 1:1 to 10:1. The total amount of EHL will be generally in the range of 2 to 40% by weight, in particular from 5 to 20% based on the total weight of the formulation.

In general, the weight ratio of the lactic acid ester solvent to the compound C is from 1:1 to 50:1.

In a preferred embodiment of the invention, the weight ratio of EHL to the compound C is from 1:1 to 50:1.

The weight ratio of compound A (component 1) and compound B (component 2) being in the range of from 1:50 to 50:1 and particularly in the range of from 1:10 to 10:1, and the weight ratio of compound A (component 1) and compound C (component 3) preferably is in the range from 1:50 to 50:1 and particularly in the range from 1:10 to 10:1.

The total pesticidally active compounds A, B and C concentrations in the ready-to-use composition formulation can be varied within substantial ranges. In general, they are in the range from 0.01 and 80% by weight, frequently in the range from 0.1 to 50% by weight, preferably in the range from 0.5 and 20% by weight, based on the total weight of the preparation.

Unless indicated otherwise, all amounts in % by weight refer to the weight of the total composition (or formulation).

According to a further particular embodiment, the composition of the present invention is a seed treatment formulation. The compositions of the present invention show good adhesion of the active compounds A, B and C to the seeds and seeds treated with the compositions of the present invention which show good flowability. Germination of the treated seeds is not affected.

The present invention also relates to the use of a composition as defined herein for treating seed.

The present invention also relates to a method of treating seed with a composition described herein, which comprises applying an effective amount of a composition as defined herein to a lot of seeds.

Seed suspoemulsion compositions comprising binders, fillers and/or plasticizers are well known in the art. Seed suspoemulsion compositions are disclosed, for example, in U.S. Pat. Nos. 5,939,356, 5,882,713, 5,876,739, 5,849,320, 5,834,447, 5,791,084, 5,661,103, 5,622,003, 5,580,544, 5,328,942, 5,300,127, 4,735,015, 4,634,587, 4,383,391, 4,372,080, 4,339,456, 4,272,417 and 4,245,432, among others.

The amount of the active compounds A, B and C that is included in the seed suspoemulsion composition according to the present invention will vary depending upon the type of seed, but the suspoemulsion composition will contain an amount of the active compounds that is pesticidally effective. In general, the amount of the active compounds in the suspoemulsion composition will range from about 0.005 to about 75% of the total weight. A more preferred range for the active compounds is from about 0.01 to about 40%; more preferred is from about 0.05 to about 20%.

The exact amount of the active compounds that is included in the suspoemulsion composition must not inhibit germination of the seed and should be efficacious in protecting the seed and/or the plant during that time in the target pest's life cycle in which it causes injury to the seed or plant. In general, the suspoemulsion will be efficacious for approximately 0 to 120 days, preferably for approximately 0 to 60 days, after sowing.

As used herein, the term "seed" denotes any resting stage of a plant that is physically detached from the vegetative stage of a plant and/or may be stored for prolonged periods of time and/or can be used to regrow another plant individual of the same species. Here, the term "resting" refers to a state wherein the plant retains viability, within reasonable limits, in spite of the absence of light, water and/or nutrients essential for the vegetative (i.e. non-seed) state. In particular, the term refers to true seeds but does not embraces plant propagules such as suckers, corms, bulbs, fruit, tubers, grains, cuttings and cut shoots.

As used herein, the term "plant" means an entire plant or parts thereof. The term "entire plant" refers to a complete plant individual in its vegetative, i.e. non-seed stage, characterized by the presence of an arrangement of roots, shoots and foliage, depending on the developmental stage of the plant also flowers and/or fruits, all of which are physically connected to form an individual which is, under reasonable conditions, viable without the need for artificial measures. The term may also refer to an entire plant harvested as such.

The term "plant parts" refers to roots, shoots, foliage, flowers or other parts of the vegetative stage of the plant, which, when dislodged and disconnected from the rest, are incapable of survival, unless supported by artificial measures or able to regrow the missing parts to form an entire plant. As used herein, fruits are also considered as plant parts.

As used herein, the term "root" refers to parts of a plant which are normally, in order to fulfill their physiological functions, located beneath the soil surface. Preferably, the term denotes the parts of a plant which are below the seed and have directly emerged from the latter, or from other roots, but not from shoots or foliage.

As used herein, the "shoots and foliage" of a plant are to be understood to be the shoots, stems, branches, leaves and other appendages of the stems and branches of the plant after the seed has sprouted, but not including the roots of the plant. It is preferable that the shoots and foliage of a plant be understood to be those non-root parts of the plant that have grown from the seed and are located a distance of at least one inch away from the seed from which they emerged (outside the region of the seed), and more preferably, to be the non-root parts of the plant that are at or above the surface of the soil.

As used herein, "fruits" are considered to be the parts of a plant which contain seeds and/or serve to spread seeds, and/or which may be removed from a plant without impairing its viability.

According to the present invention, the seed treatment comprises applying a composition of the invention to a seed. Although the present method can be applied to a seed in any physiological state, it is preferred that the seed be in a sufficiently durable state that it incurs no significant damage during the treatment process. Typically, the seed is a seed that has been harvested from the field; removed from the plant; and/or separated from the fruit and any cob, pod, stalk, outer husk, and surrounding pulp or other non-seed plant material. The seed is preferably also biologically stable to the extent that the treatment would cause no biological damage to the seed. In one embodiment, for example, the treatment can be applied to seed that has been harvested, cleaned and dried to a moisture content below about 15% by weight. In an alternative embodiment, the seed can be one that has been dried and then primed with water and/or another material and then re-dried before or during the treatment with a composition of the invention.

According to a preferred embodiment of the invention, the seed to be treated is thus substantially dry. "Substantially dry" seed includes seed that has a moisture content which results if the seed is allowed to equilibrate in an air atmosphere at 20 to 30° C. and 30-90% relative humidity, e.g. at 25° C. and 50% relative humidity.

Here, "seed treatment" refers to all methods that bring seeds and a composition of the invention into contact with each other, and "seed dressing" to methods of seed treatment which provide the seeds with an amount of the active compounds, i.e. which generate a seed comprising the active compounds. In principle, the treatment can be applied to the seed at any time from the harvest of the seed to the sowing of the seed. The seed can be treated immediately before, or during, the planting of the seed, for example using the "hopper-box" or "planter-box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "unsown seed" is meant to include seed at any period from the harvest of the seed to the sowing of the seed in the ground for the purpose of germination and growth of the plant. Preferably, the seed is not a pregerminated seed such as a pregerminated rice seed.

When it is said that unsown seed is "treated", such treatment is not meant to include those practices in which the pesticide is applied to the soil, rather than directly to the seed.

By applying the treatment to the seed prior to the sowing of the seed the operation is simplified. In this manner, seeds can be treated, for example, at a central location and then dispersed for planting. This permits the person who plants the seeds to avoid the handling and use of the active compound and to merely handle and plant the treated seeds in a manner that is conventional for regular untreated seeds, which reduces human exposure.

Specifically, the seed treatment follows a procedure in which the seed is exposed to the specifically desired amount of a pesticidally composition formulation as defined in the present invention. The composition of the present invention that is applied is a ready to use pesticidal formulation. Further dilution with water is not necessary for most types of application equipment. On the other hand, tank-mixing with other seed-treatment products and or dilution with water are possible if required.

The compositions according to the invention comprising the compounds A, B, C are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compositions according to the invention comprising the compounds A, B, C are particularly important in the control of a multitude of phytopathogenic fungi on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; natural rubber plants or ornamental and forestry plants, such as flowers, shrubs, broad-leaved trees or evergreens, e.g. conifers; and on the plant propagation material, such as seeds, and the crop material of these plants.

Preferably, the compositions according to the present invention, comprising compounds A, B, C are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with composition of the present invention and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A 242 236, EP-A 242 246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP A374753, WO 93/007278, WO 95/34656, EP A427529, EP A451878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (*Coeloptera*), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S. A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP A392225), plant disease resistance genes (e. g. potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvoral*). The methods for producing such genetically modified plants are generally known to the person skilled in the art and are described, e.g. in the publications mentioned above. Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e. g. Amflora® potato, BASF SE, Germany).

The compositions of the present invention are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. alternata*), tomatoes (e. g. *A. solani* or *A. alternata*) and wheat; *Aphanomyces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B. sorokiniana*) on cereals and e.g. *B. oryzae* on rice and turfs; *Blumeria* (formerly *Erysiphe*) graminis (powdery mildew) on cereals (e. g. on wheat or barley); *Botrytis cinerea* (teleomorph: *Botryotinia fuckeliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn (e.g. Gray leaf spot: *C. zeae-maydis*), rice, sugar beets (e. g. *C. beticola*), sugar cane, vegetables, coffee, soybeans (e. g. *C. sojina* or *C. kikuchii*) and rice; *Cladosporium* spp. on tomatoes (e. g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola*: Anthracnose stalk rot), soft fruits, potatoes (e. g. *C. coccodes*: black dot), beans (e. g. *C. lindemuthianum*) and soybeans (e. g. *C. truncatum* or *C. gloeosporioides*); *Corticium* spp., e.g. *C. sasakii* (sheath blight) on rice; *Corynespora cassiicola* (leaf spots) on soybeans and ornamentals; *Cycloconium* spp., e.g. *C. oleaginum* on olive trees; *Cylindrocarpon* spp. (e. g. fruit tree canker or young vine decline, teleomorph: *Nectria* or *Neonectria* spp.) on fruit trees, vines (e.g. *C. liriodendri*, teleomorph: *Neonectria liriodendri*: Black Foot Disease) and ornamentals; *Dematophora* (teleomorph: *Rosellinia*) necatrix (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. triticirepentis*: tan spot), rice and turf; *Esca* (dieback, apoplexy) on vines, caused by *Formitiporia* (syn. *Phellinus*) punctata, *F. mediterranea, Phaeomoniella chlamydospora* (earlier *Phaeoacremonium chlamydosporum*), *Phaeoacremonium aleophilum* and/or *Botryosphaeria obtusa; Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, rape (e. g. *E. cruciferarum*); *Eutypa lata* (Eutypa canker or dieback, anamorph: *Cytosporina lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* on soybeans and *F. verticillioides* on corn; *Gaeumannomyces graminis* (take-all) on cereals (e. g. wheat or barley) and corn; *Gibberella* spp. on cereals (e. g. *G. zeae*) and rice (e. g. *G. fujikuroi*: Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) nivale (pink snow mold) on cereals (e. g. wheat or barley); *Microsphaera diffusa* (powdery mildew) on soybeans; *Monilinia* spp., e.g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria tritici, Septoria* blotch) on wheat or *M. fijiensis* (black Sigatoka disease) on bananas; *Peronospora* spp. (downy mildew) on cabbage (e. g. *P. brassicae*), rape (e. g. *P. parasitica*), onions (e. g. *P. destructor*), tobacco (*P. tabacina*) and soybeans (e. g. *P. manshurica*); *Phakopsora pachyrhizi* and *P. meibomiae* (soybean rust) on soybeans; *Phialophora* spp. e.g. on vines (e. g. *P. tracheiphila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), potatoes and tomatoes (e. g. *P. infestans*: late blight) and broad-leaved trees (e. g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers;

*Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or, rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, and asparagus (e. g. *P. asparagi*); *Pyrenophora* (anamorph: *Drechslera*) *tritici-repentis* (tan spot) on wheat or *P. teres* (net blotch) on barley; *Pyricularia* spp., e.g. *P. oryzae* (teleomorph: *Magnaporthe* grisea, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e.g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorm*) and soybeans (e. g. *S. rolfsii* or *S. sclerotiorum*); *Septoria* spp. on various plants, e.g. *S. glycines* (brown spot) on soybeans, *S. tritici* (*Septoria* blotch) on wheat and S. (syn. *Stagonospora*) nodorum (*Stagonospora* blotch) on cereals; *Uncinula* (syn. *Erysiphe*) necator (powdery mildew, anamorph: Oidium tuckeri) on vines; *Setospaeria* spp. (leaf blight) on corn (e. g. *S. turcicum*, syn. *Helminthosporium turcicum*) and turf; *Sphacelotheca* spp. (smut) on corn, (e. g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leptosphaeria* [syn. *Phaeosphaeria] nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e. g. *U. appendiculatus*, syn. *U. phaseoli*) and sugar beets (e. g. *U. betae*); *Ustilago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

The compositions of the present invention are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae.*

The invention is illustrated by the following examples, without being limited to these.

1—Stability

The measurement of the stability of the composition of the present invention using a lactic acid ester gives the results summarized hereunder:

| Caracteristics and condition of experiment | Suspo-emulsion based on EHL | Suspo-emulsion based on RME | Suspo-emulsion based on BC |
|---|---|---|---|
| wet sieve 150 μm fresh | 0.00 | 0.00 | 0.00 |
| wet sieve after Storage 2W −10/+10 | 0.1 | 0.3% | 0.00 |
| wet sieve after Storage 8W −5/+30 | 0.1 | 0.00 | 0.9% |

In this example EHL is ethyl-hexyl-lactate, RME is methyl-oleate and BC is butylene carbonate. The wet-sieving is a standard test to check that particle size has remained constant (mesh size=150 μm). The storage regimes are as follows:

8W−5/+30=8 weeks storage in a climate chamber with temperature cycling between −5° C. and +30° C.

2W−10/+10=2 weeks storage in a climate chamber with temperature cycling between −10° C. and +10° C.

The results of the experiments above show the ability of EHL to stabilize the particles sizes distribution of the SE according to the present invention by varying the temperature of storage during a limited time of observation (between 2 to 8 weeks) compare to other solvent (REM and BC).

2—Formulation Example

Example 1a

Preparation of Solution S: Compounds A and B in EHL

To 1000 g EHL at 40° C. were added 419.3 g of Pyraclostrobin with a purity of 95.4% and 240 g Metalaxyl with a purity of 100% and 100 g Atlas G-5000 and 80 g Atlox 4914 until 1839.3 g of a clear solution S was obtained.

Example 1b

Preparation of Emulsion E 492 g of water are entered into a Silverson high-shear mixer. While shearing at 3000 rpm, 368 g of the solution S from Example 1a were added to arrive at 860 g of a milky white, free-flowing emulsion E.

Example 1c

Preparation of Dispersion D

To 175 g of water were added 274 g of triticonazole with a purity of 91% and 10 g Soprophor 4D384 and 35 g Atlox 4913 and 30 g Glycerol. This mixture is milled first on a mechanical mill (brandname PUC) and then on a bead-mill (KDL-Dynomill from Bachofen) until 90% of the particles have a size <4 μm as determined by laser-diffraction. After milling 499 g of milky-white product were recovered and were is completed with 1.4 g of a silicon antifoam, 28.5 g of a 2% solution of xanthan-gum and 1 g of the biocide Acticide MBS to arrive at 546 g of dispersion D Example 1

Preparation of Suspoemulsion

To 860 g of Emulsion E obtained in example 1b were added 185 g of Dispersion D from Example 1c to obtain 1045 g of a milky-white free-flowing suspo-emulsion.

The invention claimed is:

1. A pesticidal suspoemulsion composition comprising (i) two pesticidal compounds A and B dissolved in a lactic acid ester and wherein a) both A and B have melting points below 90° C.

b) both A and B are selected from the group consisting of pyraclostrobin, metalaxyl, mefenoxam, trifloxystrobin, imazalil, prochloraz and ipconazole with the proviso that A is different from B (ii) at least one pesticidal compound C present in solid particles, wherein said compound C has a melting point of 90° C. or above and is not fludioxonil, (iii) water, (iv) and optionally formulation auxiliaries.

2. The composition of claim 1 wherein compound A is pyraclostrobin and compound B is metalaxyl.

3. The composition of claim 1 wherein compound C is selected from the group consisting of boscalid, triticonazole and azoxystrobin.

4. The composition of claim 1 wherein the lactic acid ester is selected from the group consisting of $C_4$ to $C_{12}$ saturated and unsaturated cycloalkyl lactic acid esters and $C_4$ to $C_{12}$ saturated and unsaturated branched alkyl lactic acid esters, and mixtures thereof.

5. The composition of claim 1 wherein the lactic acid ester is selected from the group consisting of 2-ethyl hexyl lactate, cyclohexyl lactate, 2-methylcyclohexyl lactate, heptyl lactate and octyl lactate.

6. The composition of claim 1 wherein the lactic acid ester is 2-ethyl-hexyl lactate (EHL).

7. The composition of claim 1 wherein the weight ratio between the lactic acid ester and the sum of compounds A and B is from 1:1 to 10:1.

8. The composition of claim 1 wherein the weight ratio between the lactic acid ester and the compound C is from 1:1 to 50:1.

9. A method for preparing the pesticidal suspoemulsion of claim 1 comprising a) dissolving compounds A and B in the lactic acid ester resulting in a preformed solution S b) and mixing S with the compound C, water and, if present, the formulation auxiliaries.

10. A method for combating phytopathogenic fungi and/or increasing the health of plants, which comprises treating plants, seed, soil or habitat of plants with the pesticidal suspoemulsion composition of claim 1.

11. The method of claim 10 wherein compound A is pyraclostrobin and compound B is metalaxyl.

12. The method of claim 10 wherein compound C is selected from the group consisting of, boscalid, triticonazole and azoxystrobin.

13. The method of claim 10 wherein the lactic acid ester is selected from the group consisting of $C_4$ to $C_{12}$ saturated and unsaturated cycloalkyl lactic acid esters and $C_4$ to $C_{12}$ saturated and unsaturated branched alkyl lactic acid esters, and mixtures thereof.

14. The method of claim 10 wherein the lactic acid ester is selected from the group consisting of 2-ethyl hexyl lactate, cyclohexyl lactate, 2-methylcyclohexyl lactate, heptyl lactate and octyl lactate.

15. The method of claim 10 wherein the lactic acid ester is 2-ethyl-hexyl lactate (EHL).

16. The method of claim 10 wherein the weight ratio between the lactic acid ester and the sum of compounds A and B is from 1:1 to 10:1.

17. The method of claim 10 wherein the weight ratio between the lactic acid ester and the compound C is from 1:1 to 50:1.

18. A method for combating or protecting against phytopathogenic fungi which comprises treating plant propagation material with the pesticidal suspoemulsion composition of claim 1.

19. A method for combating or protecting against phytopathogenic fungi which comprises contacting a seed with an effective amount of the pesticidal suspoemulsion composition of claim 1.

20. A seed treated with the suspoemulsion composition of claim 1.

* * * * *